US009795738B2

United States Patent
Steil et al.

(10) Patent No.: US 9,795,738 B2
(45) Date of Patent: *Oct. 24, 2017

(54) INTELLIGENT THERAPY RECOMMENDATION ALGORITHIM AND METHOD OF USING THE SAME

(71) Applicant: MEDTRONIC MINIMED, INC., Northridge, CA (US)

(72) Inventors: Garry M. Steil, Boston, MA (US); Antonios Panteleon, Nea Pendeli (GR)

(73) Assignee: Medtronic MiniMed, Inc., Northridge, CA (US)

( * ) Notice: Subject to any disclaimer, the term of this patent is extended or adjusted under 35 U.S.C. 154(b) by 159 days.

This patent is subject to a terminal disclaimer.

(21) Appl. No.: 14/708,283

(22) Filed: May 10, 2015

(65) Prior Publication Data

US 2015/0238694 A1    Aug. 27, 2015

Related U.S. Application Data

(63) Continuation of application No. 11/470,585, filed on Sep. 6, 2006, now Pat. No. 9,056,165.

(51) Int. Cl.
*A61M 5/172* (2006.01)
*A61M 5/142* (2006.01)

(52) U.S. Cl.
CPC ....... *A61M 5/1723* (2013.01); *A61M 5/14244* (2013.01); *A61M 2205/18* (2013.01); *A61M 2205/502* (2013.01); *A61M 2205/52* (2013.01); *A61M 2230/201* (2013.01)

(58) Field of Classification Search
CPC ............ A61M 5/1723; A61M 2205/52; A61M 2205/502; A61M 2230/201; A61M 2205/18
See application file for complete search history.

(56) References Cited

U.S. PATENT DOCUMENTS

| 4,755,173 A | 7/1988 | Konopka et al. |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,822,715 A | 10/1998 | Worthington et al. |
| 5,925,021 A | 7/1999 | Castellano et al. |
| 5,954,643 A | 9/1999 | Van Antwerp et al. |
| 5,956,501 A | 9/1999 | Brown |

(Continued)

*Primary Examiner* — Bradley Osinski
(74) *Attorney, Agent, or Firm* — Medtronic MiniMed, Inc.

(57) ABSTRACT

An algorithm and method of making intelligent therapy recommendations for insulin pump parameters is described. The pump parameters include basal rates, carbohydrate-to-insulin ratios (CIR), and insulin sensitivity factors (ISF). A determination of whether a therapy recommendation should be made is based on comparing an updated recommended change with a threshold. The updated recommended change to the pump parameter is made based on a previous recommended change to the pump parameter and the difference between a current blood glucose value and a targeted blood glucose level. The algorithm and method confirms the therapy recommendation is within safety parameters before displaying the therapy recommendation.

4 Claims, 4 Drawing Sheets

(56) References Cited

U.S. PATENT DOCUMENTS

| | | | |
|---|---|---|---|
| 6,017,328 A | 1/2000 | Fischell et al. |
| 6,186,982 B1 | 2/2001 | Gross et al. |
| 6,233,539 B1 | 5/2001 | Brown |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,572,542 B1 | 6/2003 | Houben et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,167,818 B2 | 1/2007 | Brown |
| 7,204,823 B2 * | 4/2007 | Estes ............... A61M 5/14244 604/65 |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2003/0028089 A1 | 2/2003 | Galley et al. |
| 2003/0208113 A1 | 11/2003 | Mault et al. |
| 2005/0049179 A1 * | 3/2005 | Davidson ............... A61K 38/28 703/11 |
| 2005/0171503 A1 | 8/2005 | Van Den Berghe et al. |
| 2005/0272640 A1 | 12/2005 | Doyle, III et al. |
| 2006/0137695 A1 * | 6/2006 | Hellwig ............. G01N 33/66 128/898 |
| 2006/0272652 A1 | 12/2006 | Stocker et al. |
| 2006/0276771 A1 | 12/2006 | Galley et al. |
| 2007/0123819 A1 | 5/2007 | Mernoe et al. |
| 2009/0234213 A1 | 9/2009 | Hayes et al. |
| 2010/0138197 A1 | 6/2010 | Sher |
| 2010/0160861 A1 | 6/2010 | Causey, III et al. |

* cited by examiner

INTELLIGENT THERAPY RECOMMENDATION ALGORITHIM AND METHOD OF USING THE SAME

RELATED APPLICATIONS

This application is a continuation application of U.S. patent application Ser No. 11/470,585 filed Sep. 6, 2006, which is herein incorporated by reference.

FIELD OF THE INVENTION

The present invention relates to diabetes management, and in particular to adjusting insulin pump parameters using blood glucose information.

BACKGROUND OF THE INVENTION

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source.

Traditionally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using pump therapy, but presently over 25% of the more than 1.12 million Type I diabetics in the U.S. are using infusion pump therapy. Although the infusion pump has improved the way insulin has been delivered, the infusion pump is limited in its ability to replicate all of the functions of the pancreas. Specifically, the infusion pump is still limited to delivering insulin based on user inputted commands and parameters and therefore there is a need to improve the pump to better simulate a pancreas based on current glucose values.

SUMMARY OF THE DISCLOSURE

The present invention relates to an algorithm and method of automatically making a therapy recommendation for an insulin pump parameter based on current blood glucose values and inputted targeted blood glucose levels. The pump parameters include basal rates, carbohydrate-to-insulin ratios (CIR), and insulin sensitivity factors (ISF). The preferred embodiments update a recommended change to the pump parameter based on a previous recommended change to the pump parameter and the difference between the blood glucose value and a target blood glucose level. The updated recommended change is compared to a threshold value, and a therapy recommendation is derived if the absolute value of the recommended change exceeds that threshold value. In addition, the algorithm confirms the therapy recommendation is within safety parameters before displaying the therapy recommendation. In preferred embodiments, the therapy recommendation is considered to be within safety parameters if the blood glucose value is relatively consistent with the blood glucose history. In still further preferred embodiments, the determination of whether blood glucose value is relatively consistent is determined by a moving standard deviation analysis.

In preferred embodiments, the blood glucose values are obtained by a continuous glucose monitor. However, in alternative embodiments, the blood glucose value can be obtained by a glucose strip meter. Still in further embodiments, various safety parameters are implemented. In preferred embodiments, limits on the therapy recommendation to a particular maximum value are implemented in certain situations. In still further embodiments, limits to an absolute maximum or absolute minimum value for the pump parameter can be implemented.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
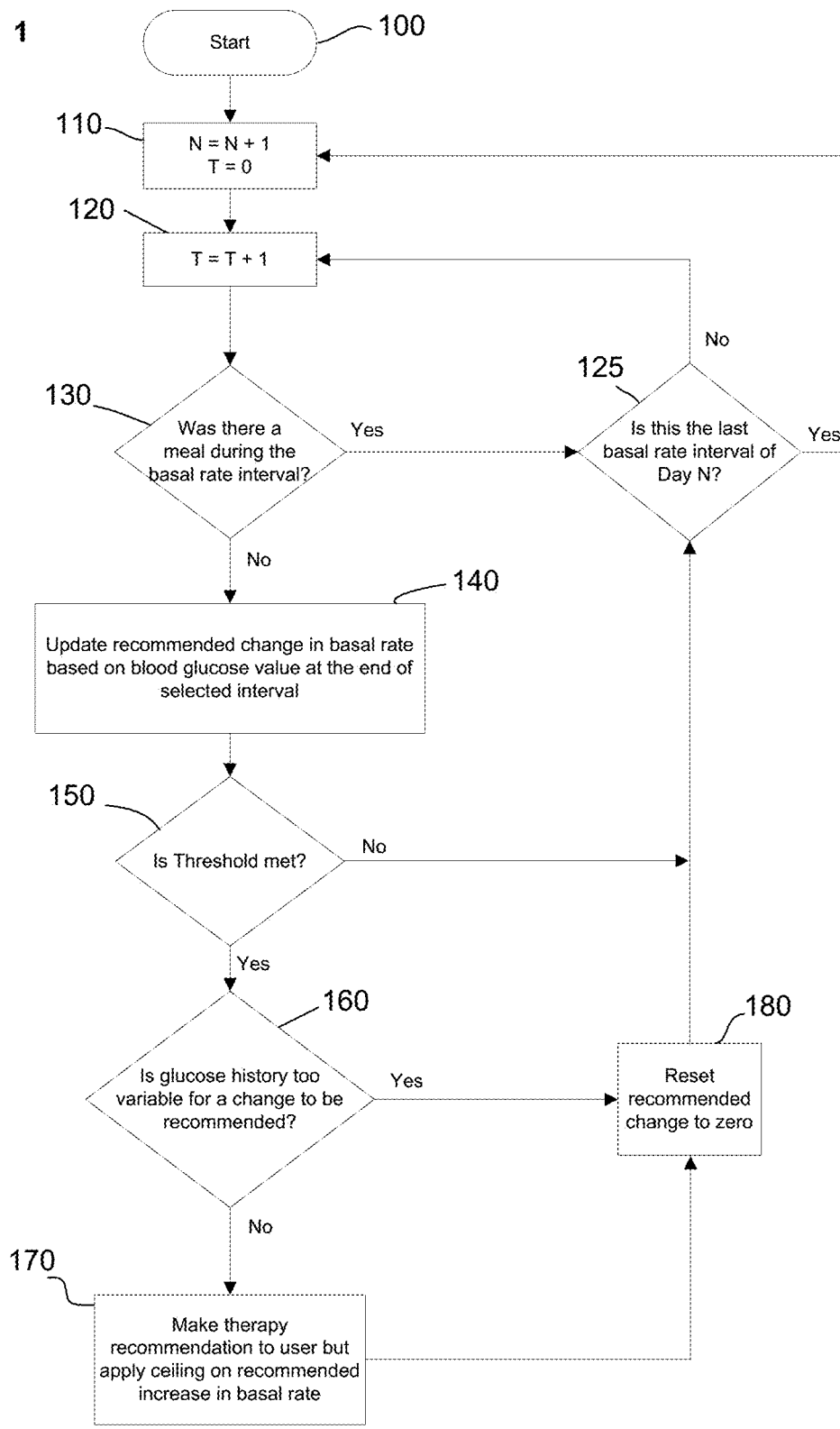
FIG. 1 is a flow chart illustrating the intelligent therapy recommendation algorithm for basal rates in accordance with the preferred embodiments of the present invention.

An insulin pump is designed to mimic the insulin delivery of a normal pancreas. To do so, an insulin pump delivers steady amounts of insulin throughout a day known as a basal rate. The basal rate on an insulin pump delivers the amount of insulin needed in the fasting state to maintain target glucose levels. The basal rate insulin is intended to account for the baseline insulin needs of the body, and makes up approximately fifty percent of the body's total daily insulin requirements. Thus, similar to the pancreas, the insulin pump delivers basal rate insulin continuously over the twenty-four hours in the day. The insulin pump can be set to provide one or more different rates during different time intervals of the day. These different basal rates at various time intervals during the day usually depend on a patient's lifestyle and insulin requirements. For example, many insulin pump users require a lower basal rate overnight while sleeping and a higher basal rate during the day, or users might want to lower the basal rate during the time of the day when they regularly exercise.

A bolus is an extra amount of insulin taken to cover a rise in blood glucose, often related to a meal or snack. Whereas a basal rate provides continuously pumped small quantities of insulin over a long period of time, a bolus provides a relatively large amount of insulin over a fairly short period of time. Most boluses can be broadly put into two categories: meal boluses and correction boluses. A meal bolus is the insulin needed to control the expected rise in glucose levels due to a meal. A correction bolus is the insulin used to control unexpected highs in glucose levels. Often a correction bolus is given at the same time as a meal bolus because patients often notice unexpected highs in glucose levels when preparing to deliver a meal bolus related to a meal.

Current insulin pumps can make bolus recommendations to the user. An example of a pump with a bolus estimator can be found in U.S. Pat. No. 6,554,798, which is incorporated by reference herein in its entirety. The bolus estimator uses three values that must be preprogrammed to perform the necessary calculations in suggesting a bolus amount. In alternative embodiments, more or fewer values may be needed or used. The inputted values needed to be stored for the bolus estimator are:

Target Blood Glucose (Target), which is the target blood glucose (BG) that the user would like to achieve and maintain. Specifically, a target blood glucose value is typically between 70-120 mg/dL for preprandial BG, and 100-150 mg/dL for postprandial BG.

Insulin Sensitivity Factor (ISF), which is a value that reflects how far the user's blood glucose drops in milligrams per deciliter (mg/dl) when one unit of insulin is taken. An example of an ISF value is 1 Unit for a drop of 50 mg/dl, although ISF values will differ from user to user.

Carbohydrate-to-Insulin Ratio (CIR), which is a value that reflects the amount of carbohydrates that are covered by one unit of insulin. An example of a CIR is 1 Unit of insulin for 15 grams of carbohydrates. Similarly, CIR values will differ from user to user.

After the above values are set in the memory of the insulin pump, the bolus estimator will suggest a bolus based on the entry of the estimated carbohydrate intake and current and target blood glucose (BG) levels. Preferred embodiments use the following equation:

$$Bolus = \frac{(CurrentBG - TargetBG)}{ISF} + \frac{CarbohydratesToBeConsumed}{CIR}$$

If the user wishes the insulin pump to suggest a bolus for the estimated carbohydrate intake only, then the only value they need to program is for the Carbohydrate Ratio, and the BG portion of the equation will be ignored. In alternative embodiments, variations or different equations may be used.

One drawback is that currently the pump parameters like ISF, CIR, and basal rates must be consistently and carefully monitored over a period of time by the diabetic individual or physician so adjustments can be made to help achieve and maintain the patient's target glucose level. For example, if fasting morning glucose is systematically higher than the target glucose level set by a health care provider or the diabetic individual himself then the overnight basal rate must be adjusted. In addition, even after the pump parameters are set, a patient's body or behavior pattern can change such that additional changes to the pump parameters are needed. These changes require a great deal of record keeping and analysis to determine how much a parameter should be changed. The difficulty in making these changes results in slow implementation of making any changes to these pump parameters. These modifications are even more difficult when the blood glucose readings are only derived from finger stick measurements. It is often difficult and uncomfortable during this trial-and-error process for patients to consistently monitor their blood glucose over a period of time and then analyze the pattern of those glucose levels. For example, a common procedure for currently adjusting basal rates is for a patient to test blood glucose levels with finger sticks at eight different times of the day including one in the middle of the night at 3 a.m. Adjustments are made to the basal rate and then the procedure is repeated every day while making adjustments until blood glucose values no longer fluctuate greatly.

Blood glucose monitors, such as the blood glucose monitor described in U.S. Pat. No. 6,809,653, which is incorporated herein in its entirety, have improved many aspects of monitoring blood glucose levels without the need for as many finger sticks, and giving a continuous glucose data that can give a better picture of exactly how the glucose levels change throughout the day. However, the data produced by the blood glucose monitors have been independently used in conjunction with the delivery of insulin using the infusion pump. There has always been a need for an intermediary such as a physician or the user themselves to act upon the blood glucose data and determine the need for changes to pump parameters. The present invention provides an improved method for monitoring and adjusting insulin pump parameters using blood glucose information obtained either through a glucose meter or a continuous glucose monitor.

According to an embodiment of the invention, an algorithm provides intelligent therapy recommendations for various pump therapy parameters to help patients more easily adjust those parameters to achieve and maintain a target blood glucose level. The algorithm automatically recommends adjustments to insulin pump parameters based on the difference between a glycemic target and actual glucose measurements.

In the preferred embodiments, the algorithms are incorporated in an insulin infusion pump that is able to receive signals from a glucose monitor, an arrangement seen in the MiniMed Paradigm® Real Time Insulin Pump and Continuous Glucose Monitoring System, which is incorporated herein by reference in its entirety. In the preferred embodiments, the algorithms are stored in the infusion pump's firmware, but can be stored in a separate software routine in the pump's ROM memory. In addition, the infusion pump controller is able to run the algorithms to perform the necessary steps to provide intelligent therapy recommendations for various pump therapy parameters. Alternatively, these algorithms can be run on a separate device such as a PDA, smart phone, computer, or the like. In further alternative embodiments, the algorithms can be run on the continuous glucose monitor or combination glucose monitor/infusion pump device or peripheral controller. In preferred embodiments, the intelligent therapy recommendations are displayed on the insulin pump, whether the recommendations themselves were calculated by the pump controller or sent from another device either by cable or wireless means. However, in alternative embodiments, the therapy recommendations can also be given on any associated device such as a glucose monitor display, a handheld PDA or smartphone, a computer, etc.

Basal Rate

Figure 4:
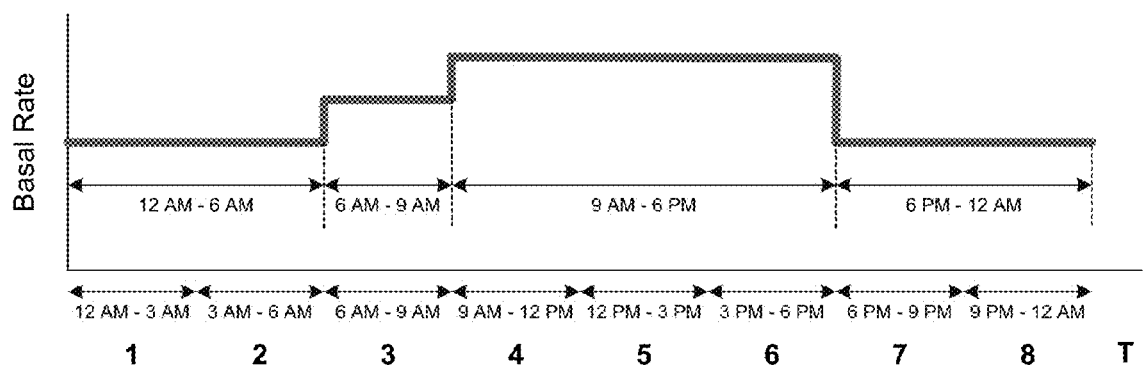
FIG. 4 is an example of a basal rate profile broken up into three hour intervals in accordance with the preferred embodiments of the present invention.

FIG. 1 describes an algorithm used to make adjustment recommendations to a basal rate in accordance with the preferred embodiments of the present invention. The algorithm of FIG. 1 can be used for both overnight basal rates and daytime basal rates. The algorithm begins at block 100. Block 110 is used to apply the algorithm to the current day N, and the basal rate interval T is set to 0. Each day can be broken up into T number of basal rate intervals where the blood glucose level is recorded at the end of each of the intervals. In the preferred embodiments, the interval is set to three hours so the glucose values are checked at the end of every three-hour interval throughout the day. For example, one basal rate interval T might be from 3 a.m. to 6 a.m. so the basal rate for that interval will be adapted based on the glucose value at 6 a.m., and the next interval will be from 6 a.m. to 9 a.m. where the glucose value at 9 a.m. is used. An example of a basal rate profile broken up into three hour intervals is seen in FIG. 4, where T is represents intervals 1-8. As seen in FIG. 4, a basal rate profile can have various basal rates throughout the day, and the basal rates do not necessarily change at each interval. Based on the running of the algorithm in FIG. 1, adjustments to the specific basal rates can be made for each time interval. One of skill in the art will appreciate that these intervals can be started at anytime to match the user's schedule and intervals can be greater or less than 3 hours in length. Potentially, the basal rate interval can be as short as the minimum programmable basal rate interval by an insulin pump (e.g. every 30 minutes on a MiniMed Paradigm® Pump) or have a maximum of having one single interval of 24 hours. Block 120 is used to apply the algorithm to each basal rate interval T during day N. The algorithm at block 130 then determines if there was a meal or correction bolus during the basal rate interval T. A meal or correction bolus changes glucose levels unrelated to the basal rate, and so the algorithm proceeds to the next interval because the meal or correction bolus interferes with the analysis required for basal rate calculation. Referring back to block 130, if there was a meal or correction bolus during interval T, the algorithm checks to see if T was the last interval of the day at block 180 and proceeds to the next interval T+1 at block 120 to compare the next time interval. If T was the last interval of the day, then the algorithm moves to the next day at block 110.

If there was no meal or correction bolus, then at block 140 a recommended change in basal rate is calculated based on the blood glucose value at the end of the selected basal rate interval. In our preferred embodiment this step uses an error integration equation:

$$\Delta I_{B_T}^N = \Delta I_{B_T}^{N-1} + K_I (BG_T - \text{Target})$$

The first step in the error integration equation is to subtract the target glucose level (Target) from the actual glucose level ($BG_T$) at the end of the basal rate interval T. The difference between those values is then multiplied by a constant ($K_I$) which is an integral gain coefficient. It determines how fast the algorithm will respond to a glucose concentration over or under the target glucose level. $K_I$ is likely linked to the total insulin requirements of the patient as well as age, gender, and other patient specific parameters, and can be adjusted employing Bayesian statistics once studies of insulin delivery in various segments of the population are performed. $K_I$ may also differ depending on the prevailing glucose level (e.g., $K_I$ may be higher for adjustments to hypoglycemia than hyperglycemia). The result of the multiplication of $K_I$ and the blood glucose difference is known as the scaled error. This scaled error is then added to the last known proposed change for that particular basal rate interval ($\Delta I_{B_T}^{N-1}$) resulting in the new proposed change to the basal rate for that time interval ($\Delta I_{B_T}^N$). For example, if the basal rate for the interval 3 a.m. to 6 a.m. on Day 70 was being analyzed then the $BG_T$ would be the glucose value at 6 a.m. Next, the scaled error from the 3 a.m. to 6 a.m. basal rate interval of Day 70 would be added to the recommended change from the 3 a.m. to 6 a.m. basal rate interval of Day 69.

At block 150, the algorithm compares the absolute value of the recommended change calculated at block 140 to a predefined threshold, typically 0.05 or 0.1 U/h. If the absolute value of the recommended change is less than the predefined threshold, then the algorithm goes to block 125 to move on to the next interval or the next day. However, if the recommended change is greater than the predefined threshold, then the recommendation is evaluated for safety at block 160. In preferred embodiments the safety review of block 160 makes sure that the glucose history is not too variable for a therapy recommendation to be made. A therapy recommendation should only be made if there is a consistent pattern in blood glucose levels to provide a certain level of confidence in the proposed therapy recommendation. In the preferred embodiments, the algorithm determines the variability of the glucose history by using the moving standard deviation, which is the standard deviation of a cluster of the most recent data. The moving standard deviation (mSTD(BG)) is compared against the difference between the average glucose value ($BG_{avg}$) and the targeted blood glucose (Target). If the glucose history is too variable for a therapy recommendation to be made (e.g. mSTD(BG) >$BG_{avg}$-Target), then no therapy recommendation is made to the user and the logic proceeds to block 180, where the recommended change is reset (e.g. $\Delta I_{B_T}^N$ is reset to zero). The algorithm then proceeds from block 180 to block 125 to determine if there is another basal rate interval that day, and then analyzes the next basal rate interval or moves to the next day. In alternative embodiments, the safety check is only applied for increases in the basal rate because the immediate risks of hypoglycemia are much greater than hyperglycemia. Hypoglycemia can cause a person to pass out in 15 or 30 minutes while it takes hours for the severe effects of hyperglycemia to become evident and cause problems.

On the other hand, if the glucose history is not too variable for a therapy recommendation to be made at block 160 (e.g. mSTD(BG)<$BG_{avg}$-Target), then the algorithm proceeds to block 170 where a therapy recommendation is made to the user. Although the therapy recommendation is tied to the final recommended change calculation that exceeds the threshold, the two values are not necessarily equal. For example, in one embodiment, the therapy recommendation can be preset to a particular value (e.g. 0.1 Units/hour) such that the therapy recommendation is made when the recommended change exceeds the threshold regardless of what the recommended change value is finally derived. The therapy recommendation can be displayed on the infusion pump display and/or combined with different alarms such as vibration, audio, etc. In the preferred embodiments, if the therapy recommendation is for an increase in the basal rate, the therapy recommendation made to the user in block 170 is capped at a particular maximum as an additional safety precaution. In preferred embodiments, the maximum therapy recommendation increase in basal rate is set at 0.1 Unit/hour for an overnight basal rate and 0.2 Unit/hour for daytime basal rate. In alternative embodiments, the maximum therapy recommendation can be set at a higher or lower value. Also, in alternative embodiments, limits on large decreases in the basal rate can be implemented or upper and lower boundaries for the overall basal rate in addition to limits on the size of changes to the basal rate can be used.

Additionally, in preferred embodiments, the therapy recommendation is always rounded to the nearest 0.1 or 0.05 U/h because this is the smallest incremental change currently possible for the MiniMed Paradigm® pumps and other insulin pumps. In alternative embodiments, the therapy recommendation may be rounded to the nearest 0.025 U/h as future pumps allow for smaller incremental changes. After a therapy recommendation is or is not made to the user at block 170, the algorithm resets the recommended change (e.g. $\Delta I_{B_T}^N$ is set to zero). The algorithm does not depend on the user accepting or rejecting the therapy recommendation since the recommended change is reset regardless. The algorithm then advances to block 125 to determine if there is another basal rate interval that day. If the basal rate interval at block 125 is not the last one of the day then the algorithm advances to the next basal rate interval of the day at block 120. If it is the last basal rate interval of the day then the algorithm proceeds to the next day at block 110 where the process begins again.

Although the above description was applied to a single daily basal rate profile (or "basal delivery pattern" or "personal delivery pattern" as used synonymously in the industry), in alternative embodiments, the algorithms can be applied to situations where the insulin pump has multiple basal rate profiles. Specifically, the algorithm can be used to make recommended changes to basal rate profile A by comparing basal rate profile A with only previous basal rate profile A, and making recommended changes to basal rate profile B by comparing basal rate profile B with only previous basal rate profile B, etc.

Carbohydrate-to-Insulin Ratio (CIR)

Figure 2:
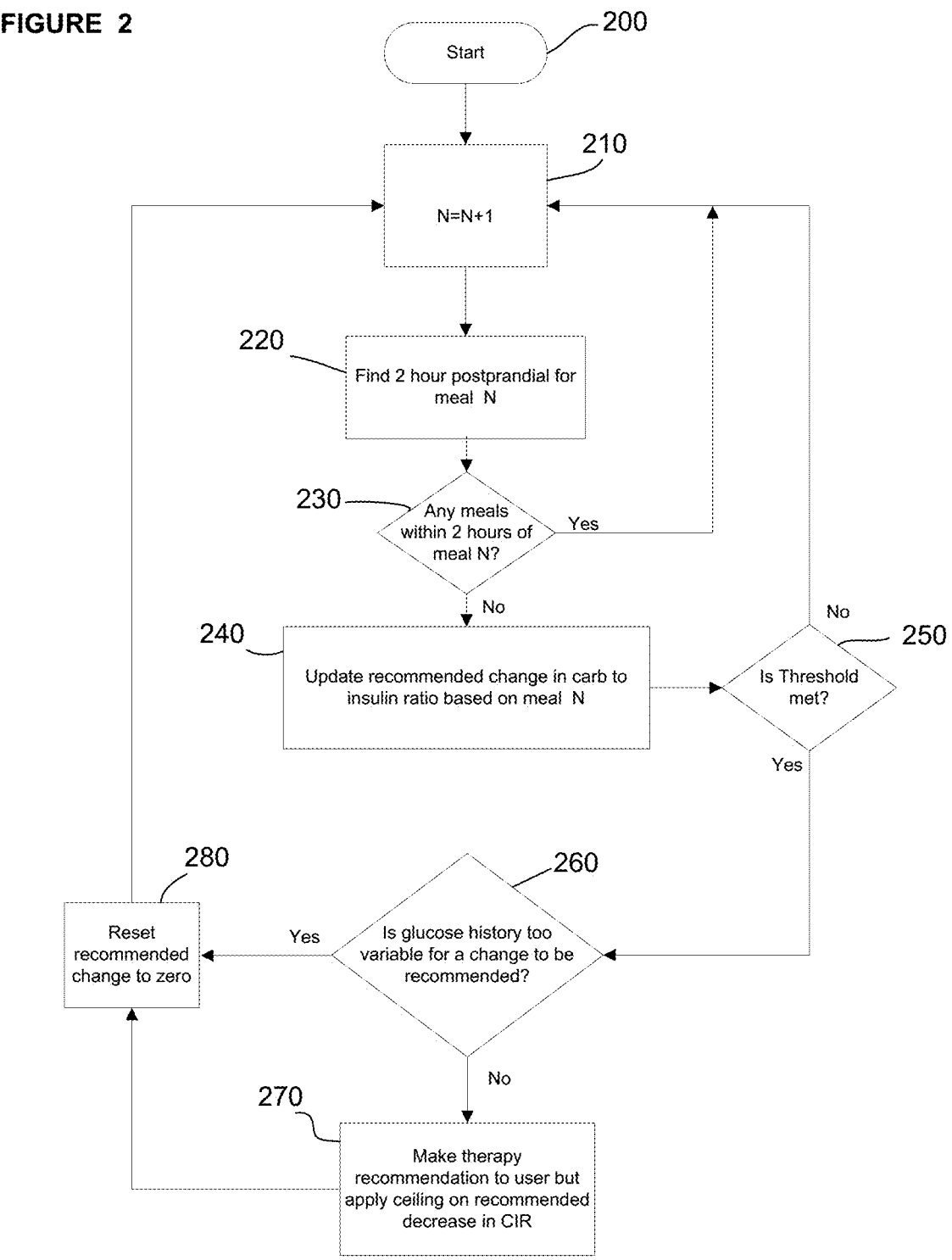
FIG. 2 is a flow chart illustrating the intelligent therapy recommendation algorithm for carbohydrate to insulin ratio in accordance with the preferred embodiments of the present invention.

FIG. 2 describes an algorithm used to make adjustment recommendations to a carbohydrate-to-insulin ratio (CIR) in accordance with the preferred embodiments of the present invention. The algorithm begins at block 200, where the algorithm reviews the postprandial blood glucose values after each meal before making or not making a recommended change to the CIR. Block 210 sets the counter variable so that the algorithm applies to the current meal N, In preferred embodiments, the algorithm at block 220 finds the glucose level two hours after meal N. Theoretically, two hours is the ideal time to measure the postprandial blood glucose value, but a longer or shorter time can be used. After the postprandial blood glucose value for meal N is retrieved, the algorithm at block 230 considers whether another meal was consumed during the two hours after meal N. In the preferred embodiments, the algorithm searches for meal or error codes within 2 hours after the last meal event, but this interval can be greater or less than 2 hours in length. A meal or error code changes glucose levels unrelated to the CIR, and so the algorithm proceeds to the next meal because the meal or error code interferes with the analysis required for CIR calculation. If there was a meal or error code, the algorithm skips the calculation for meal N and goes to block 210 to consider the next meal or move to the next day. If no meal was consumed within two hours of the last meal, the algorithm proceeds to block 240.

At block 240 a recommended change in the CIR is calculated based on the postprandial blood glucose value. In our preferred embodiment this step uses an error integration equation:

$$\Delta CIR^N = \Delta CIR^{N-1} - K_{I_{CIR}} \cdot (BG_{2h\_POST} - Target)$$

The first step in the error integration equation is to subtract the target glucose level (Target) from the actual glucose level ($BG_{2h\_POST}$) two hours after the meal. The difference between those values is then multiplied by a constant ($K_{I_{CIR}}$) which is the integral gain coefficient for CIR. $K_{I_{CIR}}$ determines how fast the algorithm will respond to a glucose concentration over or under the target glucose level. $K_{I_{CIR}}$ is likely linked to the total insulin requirements of the patient as well as age, gender, and other patient specific parameters, and can be adjusted employing Bayesian statistics once studies of insulin delivery in various segments of the population are performed. $K_{I_{CIR}}$ may also differ depending on the prevailing glucose level (e.g., $K_{I_{CIR}}$ may be higher for adjustments to hypoglycemia than hyperglycemia). The result of the multiplication of $K_{I_{CIR}}$ and the blood glucose difference is known as the scaled error. This scaled error is then subtracted from the last known proposed change for the CIR ($\Delta CIR^{N-1}$) resulting in the new proposed change to the CIR ($\Delta CIR^N$).

At block 250, the algorithm compares the absolute value of the recommended change calculated at block 240 to a predefined threshold, typically 5 grams carbohydrates per unit of insulin. If the absolute value of the recommended change is less than the predefined threshold, than the algorithm goes to block 210 to move on to the next meal event. However, if the recommended change is greater than the predefined threshold, then the recommendation is evaluated for safety at block 260. In preferred embodiments, the safety review of block 260 makes sure that the glucose history is not too variable for a therapy recommendation to be made. A therapy recommendation should only be made if there is a consistent pattern in blood glucose levels to provide a certain level of confidence in the proposed therapy recommendation. In the preferred embodiments, the algorithm determines the variability of the glucose history by using the moving standard deviation, which is the standard deviation of a cluster of the most recent data. The moving standard deviation (mSTD(BG)) is compared against the difference between the average glucose value ($BG_{avg}$) and the targeted blood glucose (Target). If the glucose history is too variable for a therapy recommendation to be made (e.g. mSTD(BG) >$BG_{avg}$-Target), then no therapy recommendation is made to the user and the logic proceeds to block 280, where the recommended change is reset (e.g. $\Delta CIR^N$ is reset to zero). The algorithm then proceeds from block 280 to block 210 to analyze the next meal. In alternative embodiments, the safety check is only applied for decreases in CIR because the immediate risks of hypoglycemia are much greater than hyperglycemia.

On the other hand, if the glucose history is not too variable for a therapy recommendation to be made at block 260 (e.g. mSTD(BG)<$BG_{avg}$-Target), then the algorithm proceeds to block 270 where a therapy recommendation is made to the user. Again, the therapy recommendation is not necessarily equal to the recommended change value that exceeds the threshold. The therapy recommendation can be displayed on the infusion pump display and/or combined with different alarms such as vibration, audio, etc. In the preferred embodiments, if the therapy recommendation is for a decrease in the CIR, the therapy recommendation made to the user in block 270 is capped at a particular maximum as an additional safety precaution. For example, the maximum cap could be set to not modify the current CIR by more than 10 carbohydrates for a Unit of insulin. In alternative embodiments, the maximum therapy recommendation decrease can be set at a higher or lower value. Also in alternative embodiments, limits on large increases in the CIR can be implemented or upper and lower boundaries for the overall CIR in addition to limits on the size of therapy recommendations to the CIR can also be used.

Additionally, in preferred embodiments, the therapy recommendation is always rounded to the nearest whole number for CIR because this is the smallest incremental change currently possible for the MiniMed Paradigm® pumps and other insulin pumps. After a therapy recommendation is or is not made to the user at block 270, the algorithm resets the recommended change (e.g. $\Delta CIR^N$ is reset to zero). The algorithm does not depend on the user accepting or rejecting the therapy recommendation since the recommended change is reset regardless. The algorithm then proceeds to the next meal at block 210.

Although the preferred embodiments describe an algorithm that updates the recommended change after each meal, alternative embodiments may use a loop structure to review every meal in one day before comparing the recommended change to the threshold. Thus, the recommended change will be refined after each meal in a day to have the most last recommended change compared to the preset threshold. Alternative embodiments may use a loop structure for a specific meal only, i.e. breakfast, thus refining the recommended change in CIR for breakfast only. In still further alternative embodiments, the algorithm does not have to have to limit the loop structure to a single day. For example, the algorithm can review all the meals over one week before deciding whether to make a recommendation to the change in CIR, or the algorithm can run continuously until the threshold is passed.

Insulin Sensitivity Factor (ISF)

Figure 3:
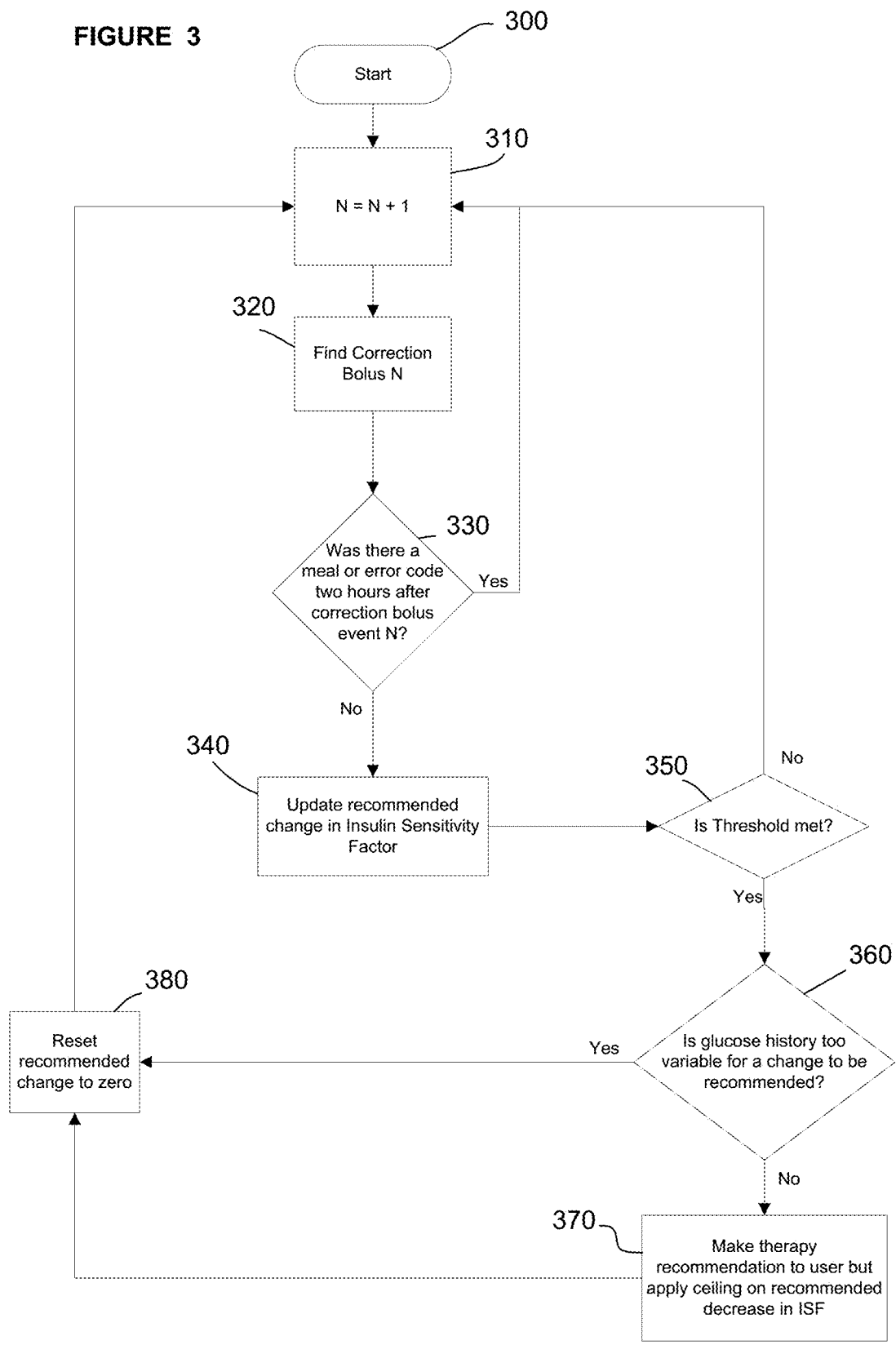
FIG. 3 is a flow chart illustrating the intelligent therapy recommendation algorithm for insulin sensitivity factor in accordance with the preferred embodiments of the present invention.

FIG. 3 describes an algorithm used to make adjustment recommendations to the insulin sensitivity factor (ISF) in accordance with the preferred embodiments of the present invention. A correction bolus is defined in this algorithm as a bolus to correct for high blood glucose values in isolation of any meal bolus. Therefore, if a bolus was taken for both a meal and to correct for high blood glucose at the same time, the bolus would not be used in this algorithm. The algorithm begins at block 300, where the algorithm reviews the blood glucose values after each correction bolus before making or not making a recommended change to the ISF. Block 310 sets the counter variable so that the algorithm applies to the current correction bolus N. In preferred embodiments, the algorithm at block 320 finds a correction bolus event N and checks the blood glucose value two hours after the correction bolus. The algorithm at block 330 then determines if there were any meals or error codes after the correction bolus event N. In the preferred embodiments, the algorithm searches for meal or error codes within 2 hours after the correction bolus event, but this interval can be greater or less than 2 hours in length. A meal or error code changes glucose levels unrelated to the ISF, and so the algorithm proceeds to the next correction bolus event because the meal or error code interferes with the analysis required for ISF calculation.

If there was no meal or error code within two hours of the correction bolus, then at block 340 a recommended change in ISF is calculated based on the blood glucose value two hours after the correction bolus. In our preferred embodiment this step uses an error integration equation:

$$\Delta ISF^N = \Delta ISF^{N-1} - K_{ISF} \cdot (BG_{2h\_POST} - \text{Target})$$

The first step in the error integration equation is to subtract the target glucose level (Target) from the actual glucose level ($BG_{2h\_POST}$) two hours after the correction bolus. The difference between those values is then multiplied by a constant ($K_{ISF}$) which is the integral gain coefficient for ISF. $K_{ISF}$ determines how fast the algorithm will respond to a glucose concentration over or under the target glucose level. $K_{ISF}$ is also linked to the total insulin requirements of the patient as well as age, gender, and other patient specific parameters, and can be adjusted employing Bayesian statistics once studies of insulin delivery in various segments of the population are performed. $K_{ISF}$ may also differ depending on the prevailing glucose level (e.g., $K_{ISF}$ may be higher for adjustments to hypoglycemia than hyperglycemia). The result of the multiplication of $K_{ISF}$ and the blood glucose difference is known as the scaled error. This scaled error is then subtracted from the last known proposed change for the ISF ($\Delta ISF^{N-1}$) resulting in the new proposed change to the ISF ($\Delta ISF^N$).

At block 350, the algorithm compares the absolute value of the recommended change calculated at block 340 to a predefined threshold, typically 5 mg/dl for a Unit of insulin. If the absolute value of the recommended change is less than the predefined threshold, then the algorithm goes to block 310 to move on to the next correction bolus event. However, if the absolute value of the recommended change is greater than the predefined threshold, then the recommendation is evaluated for safety at block 360. In preferred embodiments, the safety review of block 360 makes sure that the glucose history is not too variable for a therapy recommendation to be made. A therapy recommendation should only be made if there is a consistent pattern in blood glucose levels to provide a certain level of confidence in the proposed therapy recommendation. In the preferred embodiments, the algorithm determines the variability of the glucose history by using the moving standard deviation, which is the standard deviation of a cluster of the most recent data. The moving standard deviation (mSTD(BG)) is compared against the difference between the average glucose value ($BG_{avg}$) and the targeted blood glucose (Target). If the glucose history is too variable for a therapy recommendation to be made (e.g. mSTD(BG)>$BG_{avg}$−Target), then no therapy recommendation is made to the user and the logic proceeds to block 280, where the recommended change is reset (e.g. $\Delta ISF^N$ is reset to zero). The algorithm then proceeds from block 380 to block 310 to analyze the next correction bolus event. In alternative embodiments, the safety check is only applied for decreases in ISF because the immediate risks of hypoglycemia are much greater than hyperglycemia.

On the other hand, if the glucose history is not too variable for a therapy recommendation to be made at block 360 (e.g. mSTD(BG)<$BG_{avg}$−Target), then the algorithm proceeds to block 370 where the therapy recommendation is made to the user. Again, the therapy recommendation is not necessarily equal to the recommended change value that exceeds the threshold. The therapy recommendation can be displayed on the infusion pump display and/or combined with different alarms such as vibration, audio, etc. In the preferred embodiments, if the therapy recommendation is for an decrease in the ISF, the therapy recommendation decrease made to the user in block 370 is capped at a particular maximum as an additional safety precaution. For example, the maximum cap could be set to not modify the current ISF by more than 10 mg/dl for a Unit of insulin. In alternative embodiments, the maximum therapy recommendation decrease can be set at a higher or lower value. Also, limits on large increases in the ISF can be implemented or upper and lower boundaries for the overall ISF in addition to limits on the size of therapy recommendations to the ISF can be used.

Additionally, in preferred embodiments, the therapy recommendation is always rounded to the nearest whole number for ISF because this is the smallest incremental change currently possible for the MiniMed Paradigm® pumps and other insulin pumps. After a therapy recommendation is made to the user at block 370, the algorithm resets the recommended change (e.g. $\Delta ISF^N$ is reset to zero). The algorithm does not depend on the user accepting or rejecting the therapy recommendation since the recommended change is reset regardless. The algorithm then advances to the next correction bolus event at block 310

Although the preferred embodiments describe an algorithm that updates the recommended change after each correction bolus event, alternative embodiments may use a loop structure to review all the correction boluses in one day before comparing the recommended change to the threshold. Thus, the recommended change will be refined after each correction bolus calculation such that the last recommended change is then compared to the preset threshold. In still further alternative embodiments, the algorithm does not have to have to limit the loop structure to a single day. For example, the algorithm can review all the correction bolus events over one week before deciding whether to make a recommendation to the change in ISF, or be allowed to run continuously until the threshold is met.

Therefore, as described above, various modifications and alternatives are possible in implementing the present invention. Moreover, other alternative embodiments are possible from the above description. For example, a modified error integration formula can be substituted for the error integration formula described in the preferred embodiments. One possibility is to use the area under the glucose curve (AUC) rather than the actual glucose level (BG) at the end of interval T. For example, for purposes of basal rate, the modified error integration formula can be as follows:

$$\Delta I_{B_T}^N = \Delta I_{B_T}^{N-1} + K_I^*(AUC_T - \text{Target})$$

Additional steps and changes to the order of the algorithm can be made while still performing the key teachings of the present invention. For example, additional safety parameters can be applied as well as removed from the algorithm. In addition, in the case of concurrent algorithm recommendations, Bayesian statistics might be applied to determine the order of change in pump therapy parameters. So while the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of automatically making a therapy recommendation for adjusting a basal rate stored on an insulin pump, the method comprising the steps of:

obtaining a blood glucose value at the end of a time interval;

determining if an intervening event occurred during the time interval, wherein the intervening event changes the blood glucose value unrelated to the stored basal rate and thereby interferes with recommending a change to the stored basal rate;

recommending no change to the stored basal rate based on the blood glucose value if the intervening event occurred during the time interval;

updating a recommended change to the stored basal rate based on a previous day recommended change to the stored basal rate during that interval and the difference between the blood glucose value and a target blood glucose level if no intervening event occurred during the time interval;

comparing an absolute value of the updated recommended change to a predefined threshold value of the stored basal rate;

making no therapy recommendation if the updated recommended change does not exceed the threshold or the therapy recommendation is not within safety parameters;

making the therapy recommendation if the updated recommended change exceeds the threshold and the therapy recommendation is within safety parameters; and displaying the therapy recommendation to adjust the stored basal rate.

2. The method of claim 1, wherein the basal rate is an overnight basal rate.

3. The method of claim 1, wherein the step of recommending no change to the stored basal rate further comprises: skipping the blood glucose value if the intervening event includes a meal or a correction bolus during the time interval before the blood glucose value was obtained.

4. The method of claim 1, wherein the step of confirming the therapy recommendation is within safety parameters comprises:

reviewing recent blood glucose history; and using a moving standard deviation analysis on the recent blood glucose history to confirm the blood glucose value is relatively consistent with the blood glucose history.

* * * * *